United States Patent

Heaven et al.

Patent Number: 5,308,327
Date of Patent: May 3, 1994

[54] SELF-DEPLOYED INFLATABLE RETRACTOR

[75] Inventors: Malcolm D. Heaven, Newark; Stephen J. Shapiro, Encino, both of Calif.

[73] Assignee: Advanced Surgical Inc., Princeton, N.J.

[21] Appl. No.: 797,727

[22] Filed: Nov. 25, 1991

[51] Int. Cl.$^5$ .................................. A61H 29/00
[52] U.S. Cl. .................. 604/96; 606/192; 606/195; 128/20
[58] Field of Search ............... 128/3, 20; 606/127, 606/191–192, 195, 198; 604/96, 104–106

[56] References Cited

U.S. PATENT DOCUMENTS

| | | |
|---|---|---|
| 6,796 | 10/1949 | Haile . |
| 157,343 | 12/1874 | Molesworth . |
| 318,535 | 5/1885 | Bihler . |
| 734,498 | 7/1903 | Bachler . |
| 901,376 | 10/1908 | Roberts . |
| 923,303 | 6/1909 | Shults . |
| 1,213,005 | 1/1917 | Pillsbury . |
| 1,970,802 | 8/1934 | Johnson . |
| 2,032,859 | 3/1936 | Wappler . |
| 2,570,921 | 10/1951 | Collins ............ 154/126.5 |
| 2,667,437 | 1/1954 | Zoubek ............ 154/126.5 |
| 2,798,523 | 7/1957 | Barrett . |
| 2,847,997 | 8/1958 | Tibone ............... 128/325 |
| 2,927,584 | 3/1960 | Wallace .............. 128/349 |
| 3,048,514 | 8/1962 | Bentele et al. . |
| 3,126,307 | 3/1964 | Drittenbass ........ 156/273 |
| 3,232,810 | 2/1966 | Reesen ............. 156/273 |
| 3,417,745 | 12/1968 | Sheldon ............... 128/6 |
| 3,483,859 | 12/1969 | Pittman .......... 604/96 X |
| 3,509,883 | 5/1970 | Dibelius ............. 128/348 |
| 3,605,747 | 9/1971 | Pashkow ............ 128/303 |
| 3,712,772 | 1/1973 | Hunkar .............. 425/141 |
| 3,782,370 | 1/1974 | McDonald .......... 128/20 |
| 3,834,394 | 9/1974 | Hunter et al. ...... 128/325 |
| 3,841,304 | 10/1974 | Jones . |
| 3,841,317 | 10/1974 | Awais . |
| 3,863,639 | 2/1975 | Kleaveland ...... 128/20 X |
| 4,076,872 | 2/1978 | Lewicki et al. . |
| 4,172,301 | 10/1979 | Everard et al. . |
| 4,174,715 | 11/1979 | Hasson ............... 128/321 |
| 4,190,042 | 2/1980 | Sinnreich ............ 128/20 |
| 4,198,981 | 4/1980 | Sinnreich . |
| 4,240,433 | 12/1980 | Bordow .............. 128/347 |
| 4,268,338 | 5/1981 | Peterson ............ 156/251 |
| 4,311,146 | 1/1982 | Wonder .............. 128/325 |
| 4,312,353 | 1/1982 | Shahbabian ........ 128/344 |
| 4,393,872 | 7/1983 | Reznik et al. ....... 604/151 |
| 4,428,375 | 1/1984 | Ellman ............... 128/334 |
| 4,557,255 | 12/1985 | Goodman .............. 128/7 |
| 4,611,594 | 9/1986 | Grayhack et al. ... 128/328 |
| 4,654,028 | 3/1987 | Suma ................. 604/106 |
| 4,735,603 | 4/1988 | Goodson et al. ...... 604/21 |

(List continued on next page.)

FOREIGN PATENT DOCUMENTS

| | | |
|---|---|---|
| 490714 | 11/1991 | European Pat. Off. . |
| 2514428 | 10/1976 | Fed. Rep. of Germany . |
| 131620 | 7/1978 | Fed. Rep. of Germany . |
| 490714A1 | 6/1992 | France . |

Primary Examiner—C. Fred Rosenbaum
Assistant Examiner—Corrine Maglione
Attorney, Agent, or Firm—Burns, Doane, Swecker & Mathis

[57] ABSTRACT

A medical device such as a retractor or isolation bag including an inflatable member which expands from a collapsed configuration to an expanded configuration when pressurized gas or liquid is supplied thereto. The member can include a plurality of fluid channels, ribs and pre-shaped wire members. The device is inserted into a body cavity through a tube. The device can also be actuated by a honeycomb reinforcing structure with or without the use of pressurized fluid. The device can be manufactured by forming one or more air conduits in a member of expandable material or by enclosing a honeycomb reinforcing structure in a polymer material.

12 Claims, 7 Drawing Sheets

U.S. PATENT DOCUMENTS

| | | | |
|---|---|---|---|
| 4,739,762 | 4/1988 | Palmaz | 128/343 |
| 4,744,363 | 5/1988 | Hasson | 606/1 |
| 4,796,629 | 1/1989 | Grayzel | 604/96 X |
| 4,802,479 | 2/1989 | Haber et al. | 128/344 |
| 4,803,029 | 2/1989 | Iversen et al. | |
| 4,857,129 | 8/1989 | Jensen et al. | 156/273 |
| 4,873,978 | 10/1989 | Ginsburg | 128/345 |
| 4,875,482 | 10/1989 | Hariri et al. | 128/352 |
| 4,899,747 | 2/1990 | Garren et al. | 606/192 |
| 4,909,789 | 3/1990 | Taguchi et al. | 604/107 |
| 4,984,564 | 1/1991 | Yuen | 128/20 |
| 4,999,074 | 3/1991 | Afeyan | |
| 5,027,793 | 7/1991 | Engelhardt et al. | 128/20 |
| 5,035,232 | 7/1991 | Lutze et al. | 128/20 |
| 5,037,379 | 8/1991 | Clayman et al. | 600/37 |
| 5,074,867 | 12/1991 | Wilk | |
| 5,080,088 | 1/1992 | LeVahn | 128/20 |
| 5,143,082 | 9/1992 | Kindberg et al. | |
| 5,163,949 | 11/1992 | Bonutti | |
| 5,178,133 | 1/1993 | Pena | |
| 5,195,507 | 3/1993 | Bilweis | 128/20 |

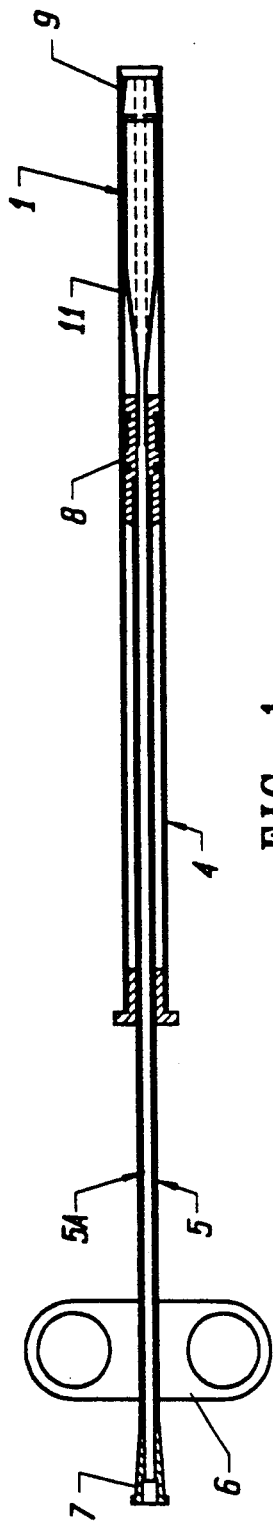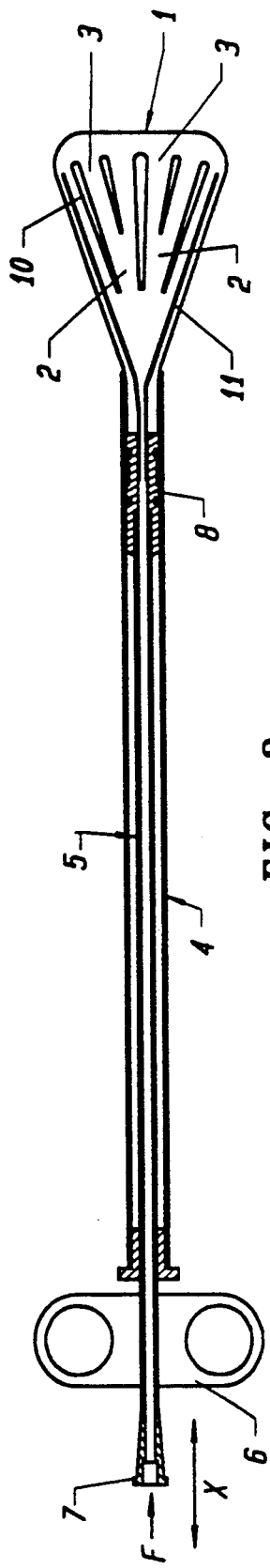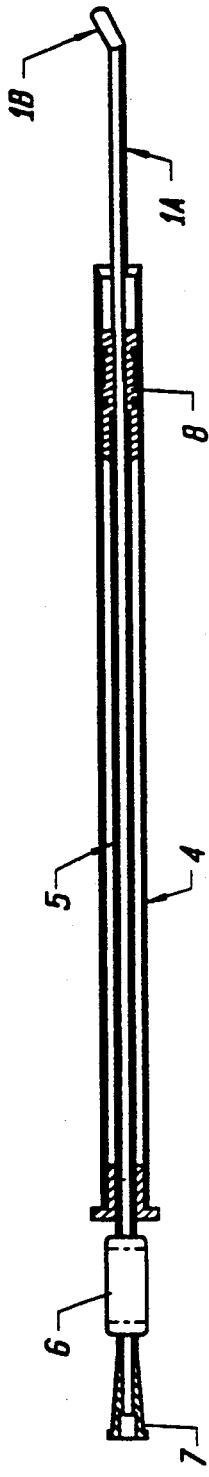
FIG. 1
FIG. 2
FIG. 3A

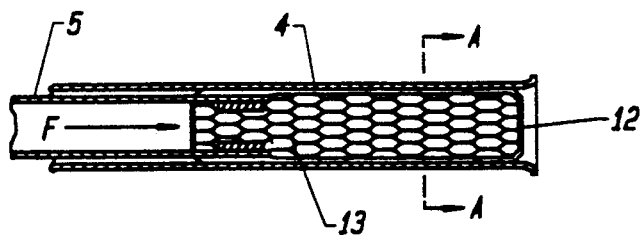
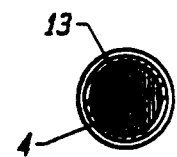
FIG. 4A   FIG. 4C
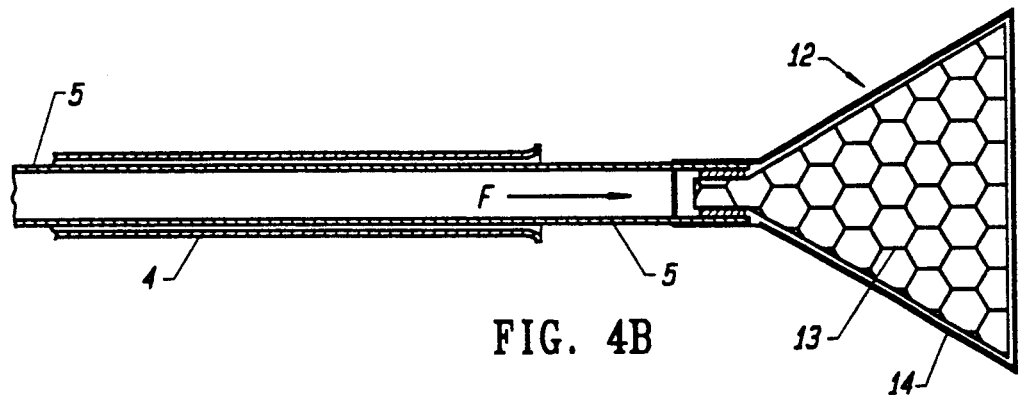
FIG. 4B
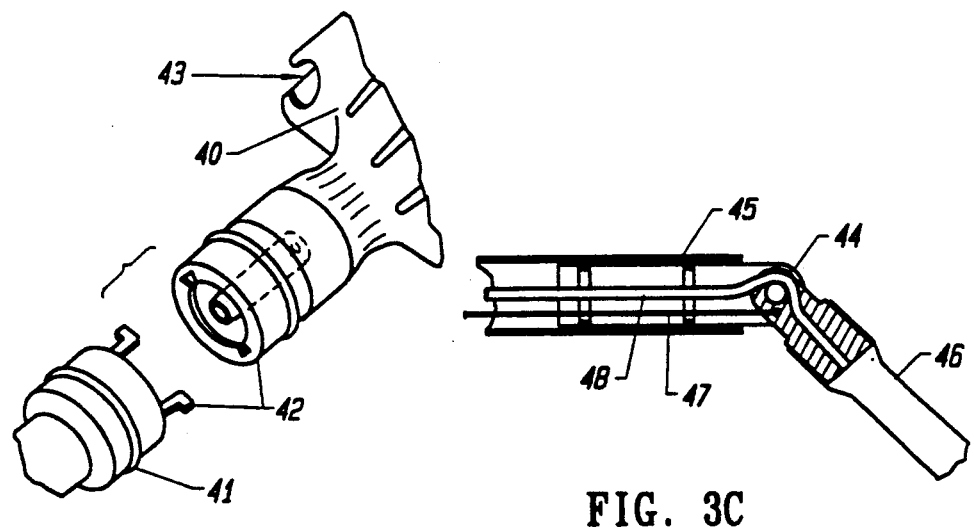
FIG. 3B   FIG. 3C

SELF-DEPLOYED INFLATABLE RETRACTOR

FIELD OF THE INVENTION

The invention relates to collapsible structures which may be self-deployed to form rigid or semi-rigid shaped medical devices such as retractors or isolation bags as well as a method of manufacture thereof. The invention further relates to collapsible structures which may be deployed and inflated either pneumatically or hydraulically to form rigid or semi-rigid medical devices.

BACKGROUND OF THE INVENTION

A number of methods have been proposed for forming retractors, among which there may be mentioned U.S. Pat. No. 4,744,363 ("Hasson"), U.S. Pat. No. 4,190,042 ("Sinnreich"), and U.S. Pat. No. 4,909,789 ("Taguchi et al."). The prior art retractors, however, possess either inadequate strength or are somewhat traumatic.

A number of methods have been proposed for forming retractors. For example, see the Hasson, Sinnreich and Taguchi et al. patents. The devices disclosed in these patents are made by methods of manufacture which tend to cause trauma to the organs they are used to move. In addition, the manufacturing techniques disclosed in these patents allow only a limited range of capabilities.

A major problem associated with minimally invasive endoscopic surgical procedures is that of removal of inflamed or diseased tissue or organs. One such procedure is the laparoscopic removal of the gangrenous gallbladder. Withdrawing the infected organ through the abdominal cavity without first isolating it risks the spread of infection and peritonitis. Currently available isolation bags are clumsy and poorly designed. A number of methods have been proposed for forming isolation bags, among which there may be mentioned U.S. Pat. No. 5,037,379 ("Clayman") and U.S. Pat. No. 4,557,255 ("Goodman"). The device disclosed in Clayman includes a net which will not prevent the transfer of diseased cells, and with the device disclosed in Goodman there is no way of ensuring the bag deploys properly or conveniently for accepting the organ or tissue.

The present invention provides solutions to the various problems noted above with respect to the prior art retractors, isolation bags and methods of manufacturing such devices.

SUMMARY OF THE INVENTION

The invention provides a medical device usable within a body cavity. The device includes a deployable inflatable and collapsible member which has a first configuration when in a collapsed state and a second configuration when in an expanded state. The member is introducible into a body cavity by passing the member through a tube while the member is in the collapsed state, and the member is expandable from the first configuration to the second configuration when the member is inserted into the cavity beyond an end of the tube. The device also includes fluid actuating means for expanding the member from the first to the second configuration. The fluid actuating means comprises a conduit supported by the member such that when pressurized gas or liquid is supplied to the conduit, the member is expanded into the second configuration. It is within the scope of the invention to include means to release and retrieve the expanded inflatable and collapsible member within the body. Other means to interdigitate released members or to articulate members are also disclosed.

According to various aspects of the invention, the member can include an atraumatic surface thereon comprising, for example, a natural rubber latex. The member itself can comprise a polymeric material such as but not limited to PVC, PVC copolymers, chlorinated polyethylene, ethylene ethyl acrylate copolymers, butadiene styrene block copolymers, polyethylene terephthalate, ionomers, polyisoprene, silicones, polyethylene, polyethylene copolymers, ethylene vinyl acetate copolymers, fluoropolymers, polyvinylidene fluoride, polyvinylidene fluoride copolymers, polypropylene, polypropylene copolymers, nylons such as but not limited to nylon 6.6, polyurethanes and other suitable polymers, blends and mixtures thereof. The member can also comprise a coated woven fabric or a coated sewn fabric. The fluid actuating means can include a plurality of fluid channels communicating with the conduit. Also, the fluid actuating means can comprise the conduit and a discrete conduit which is not in communication with the conduit whereby the conduit and the discrete conduit can each be supplied with pressurized fluid at different pressures. The member can include reinforcing means such as ribs and pre-shaped wire members.

According to one aspect of the invention, the member comprises a retractor. The device can include a tube for delivery of the retractor to a body cavity, a rod having a distal end thereof attached to a proximal end of the retractor and a passageway in the rod communicating with the conduit of the retractor for inflation thereof. The device can also include a manually operable handle on a proximal end of the rod and a sliding carrier attached to the distal end of the rod providing a seal between an inner periphery of the tube and an outer periphery of the rod.

According to another embodiment of the invention, the member can comprise an isolation bag. The device can include a wire loop extending through a neck channel around an openable end of the isolation bag with the wire being movable through the neck channel to close the openable end of the isolation bag. The wire loop of springy material as defined later herein expands the openable end of the isolation bag to an open condition. The device can include a tube for delivery of the isolation bag to a body cavity, a rod having a distal end thereof attached to a proximal end of the retractor and a passageway in the rod communicating with the conduit of the isolation bag for inflation thereof.

The invention also provides a medical device usable within a body cavity comprising a collapsible member and mechanical means for expanding the member from a first configuration when in a collapsed state to a second configuration when in an expanded state. The member can be introduced into a body cavity by passing the member through a tube while the member is in the collapsed state with the member being expandable from the first configuration to the second configuration when the member is inserted into the cavity beyond an end of the tube. The mechanical means can comprise a honeycomb reinforcing structure which is supported by the member such that in an unconfined state, such as when the member is passed outwardly of a distal end of the tube, the honeycomb reinforcing structure expands the member to its second configuration. The honeycomb reinforcing structure is resilient enough to allow the member to collapse to the first configuration, such as when the member is retracted into the tube. The expansion of the honeycomb reinforcing structure may be assisted by combining the honeycomb reinforcing structure with an inflatable member.

The mechanical means can include an atraumatic surface thereon comprising, for example, a natural rubber latex, and the member can comprise a retractor. The device can include a tube for delivery of the retractor to a body cavity and a rod having a distal end thereof attached to a proximal end of the retractor. The honeycomb reinforcing structure can include square, hexagonal or the like cells wherein cell walls of the, for example, honeycomb reinforcing structure are closer together when the member is in the first configuration than when the member is in the second configuration. The honeycomb reinforcing structure can be coated on at least one side thereof with, for example, a natural latex rubber coating. For instance, the member can be completely enclosed within the coating or a molding.

The invention also provides a method of making an inflatable medical device such as a retractor or isolation bag, comprising steps of providing a member of material which is expandable from a collapsed configuration to an expanded configuration and forming air actuating means in the member for expanding the member from the collapsed configuration to the expanded configuration when pressurized gas or liquid is supplied to the air actuating means.

According to various aspects of the method, the material can comprise sheets of polymeric material, and the forming step can comprise bonding the sheets to provide at least one conduit which is open at one end for receiving pressurized fluid and closed at another end to cause the member to expand to the expanded configuration when pressurized fluid is supplied to the open end of the conduit. The fluid actuating means can be provided by molding the member with a main supply conduit and a plurality of channels in communication with the main supply conduit. The method can include molding a plurality of strengthening ribs in the member, and/or at least one bent wire can be incorporated in the member such that the wire has its bent shape when the member is in the second configuration and the wire is deformed from its bent shape when the member is in the first configuration. The material can comprise woven or sewn fabric coated with a fluid impermeable layer such as a natural rubber latex. The forming step can be carried out by molding the member with the air actuating means being part of the molded member. The forming step can also comprise welding or sewing the material to provide the air actuating means, the method further comprising turning the member inside out to provide seams on an interior of the member.

The member can comprise an isolation bag, the forming step comprising bonding two sheets of polymeric material to form a composite and provide the air actuating means therein. The method can include a step of heating the composite and stretching the composite to form a bag corresponding to the expanded configuration. The method can also include a step of providing a neck channel around an open end of the bag and extending a wire of springy material as defined herein in the neck channel. The method can further include attaching an inflation tube to the bag such that an open end of the inflation tube communicates with the neck channel, the neck channel providing communication with the air actuating means.

BRIEF DESCRIPTION OF THE DRAWING

The invention will now be described in greater detail, by way of example, with reference to the accompanying drawing in which:

FIG. 1 shows a medical device according to the invention in the folded and stored configuration;

FIG. 2 shows the device of FIG. 1 after ejection and deployment from its storage tube;

FIG. 3a shows a side elevation of the device of FIG. 2, and demonstrates one example of a preferred shape;

FIG. 3b shows an enlarged view of an alternate embodiment having a releasable retractor connection;

FIG. 3c shows a view similar to FIG. 3b of another embodiment having an articulated retractor;

FIG. 4a shows another device according to the invention in the folded and stored configuration;

FIG. 4b shows the device of FIG. 4a after ejection from its storage tube;

FIG. 4c shows a cross-section of the device shown in FIG. 4a along the lines A—A;

FIG. 8b shows a plunger arrangement for deforming the welded structure held in the clamping device of FIG. 8a;

FIG. 8c shows how the plunger of FIG. 8b can be used to deform the welded structure of FIG. 8a.

DETAILED DESCRIPTION OF THE PREFERRED EMBODIMENTS

Figure 5A:
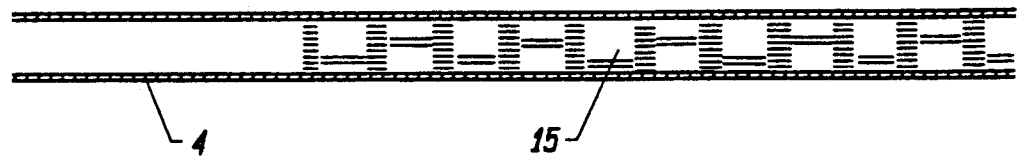
FIG. 5a shows a modification of the device shown in FIGS. 4a-c wherein the modified device is in the collapsed state.

One aspect of the invention relates to collapsible structures which may be deployed and inflated either pneumatically or hydraulically to form rigid or semi-rigid shaped medical devices. Such medical devices may, for example, be employed as retractors in minimally invasive surgical procedures such as laparoscopy. In this suggested application, the medical devices may be stored in a confined space, e.g., a small diameter tubular member. The member may then be inserted into, for example, the abdominal cavity through a device known as a trocar. Upon clearing the trocar, the expandable end of the device can be physically deployed by movement from its storage location and via inflation with a suitable medium such as air or saline solution. Upon deployment, the device assumes its preferred shape which may be, for example, similar to a spatula and can be used to safely move organs around in order to improve visualization for the surgical procedure. This example is but one possible use. It will be immediately apparent to those skilled in the art that given the multiplicity of possible shapes which may be manufactured, numerous other uses exist. For instance, the collapsible device can be a bag-shaped device for use as a containment for surgically removed tissue. In this case, the device can be inserted into, for example, the abdominal cavity through a trocar. Upon exiting the trocar the device can be physically ejected distally to the trocar and subsequently deployed via inflation with a suitable medium such as air or saline solution. Upon deployment, the device assumes its preferred bag shape and can be used to safely contain and subsequently allow withdrawal of inflamed and bacterially contaminated organs.

According to a first aspect of the invention, a collapsible, fluid actuated medical device, such as a retractor, comprising an inflated structure is provided which offers a firm but slightly yielding surface. This surface is preferably extremely atraumatic when used in contact with biological tissue. Suitable materials for the inflated section may be polymeric materials such as but not limited to PVC, PVC copolymers, chlorinated polyethylene, ethylene ethyl acrylate copolymers, butadiene styrene block copolymers, polyethylene terephthalate, ionomers, polyisoprene, silicones, polyethylene, polyethylene copolymers, ethylene vinyl acetate copolymers, fluoropolymers, polyvinylidene fluoride, polyvinylidene fluoride copolymers, polypropylene, polypropylene copolymers, nylons such as but not limited to nylon 6.6, polyurethanes and other suitable polymers, blends and mixtures thereof. The inflated section of the retractor may be manufactured via numerous polymeric forming processes. Methods which may be employed include, but are not limited to, blow-molding, injection molding, dip molding, welding from sheet or tubing using adhesives, ultrasonic welding or high frequency welding, for example, or other methods, as will be apparent to those skilled in the art.

It has also been found that complex shapes can be manufactured from woven or sewn fabric using, for example, numerically controlled knitting or weaving machines. These may then be made pressure tight by dipping in, for example, natural rubber latex. The fabric structures offer the capability of high multi-axial reinforcement and hence excellent strength and rigidity at high inflation pressures. Shapes may also be made from welded fabric and fabric composites. For example, polyethylene impregnated polyester or nylon fabric can be welded to form coherent structures using techniques apparent to those skilled in the art.

It has further been found that by virtue of changing the wall thickness of the structure selectively, for example (but not limited to) during blow-molding via parison programming using a method such as that disclosed in U.S. Pat. No. 3,712,772 ("Hunkar"), a predetermined shape can be induced in the pressurized structure, for example, a hood or a curved spatula shape. This preferred shape may also be attained via selectively varying the modulus, for example, of the two sheets being welded together where welding is being used as the fabrication method of choice. Yet a further embodiment utilizes independent inflation channels, which allows for control of shape via the use of differential inflation pressures. Other methods of providing suitable shapes to the inflated medical devices of the invention will be apparent to those skilled in the art.

It may also be mentioned that in suitable cases, it may be advantageous to employ the technique of forming the basic shape and then turning the shape inside out, for example with sewn or welded articles, so that any external seam now resides on the inside of the articles, yielding a less traumatic surface on the exterior. Additional shapes may be permitted by using a preforming operation, such as vacuum forming, prior to welding sheets together.

A further embodiment of the present invention involves preferred coatings on the device. In certain instances it may be desirable to utilize, for example, a high strength polymer for the basic device, but to impart a preferred surface characteristic via, for example, plasma activation of the surface and subsequent bonding via reaction with a monomer or active polymer or other means known to those skilled in the art. By way of example, devices manufactured from a fluorocopolymer can be treated with an active gas plasma and subsequently be coated with a thin natural rubber latex which bonds tenaciously, yielding a surface with improved organ handling capabilities. It is also possible, using the same or similar techniques, to incorporate coatings which may contain slow release drugs or topical treatments, for example, which may improve the patient's well-being during a surgical procedure.

It is further proposed in order to gain added strength and to impart various predetermined shapes to such inflated structures, that they be assisted with pre-shaped wire members. (These may be flat or round cross-section depending upon the specific needs of the retractor.) The inflated outer molding as described above envelopes and protects the organs from the strength members when maximum lifting force is used while contributing strength itself due to the high pressure liquid or gas inflation medium over a wide projected area, as opposed to a single focussed point of lifting. While offering added strength, the wires or spring sections still allow for collapsibility for delivery, deployment, and removal of the inflatable structure. These reinforcing members may be fixed at one end and their natural resistance to deformation used to deploy them, or they may be pivoted and operated via a wedge device, for example.

It is further proposed that, again in order to extend the lifting capability of inflated polymer structures, the wall of the shape may be constructed from a material that contains longitudinal reinforcing fibers. These fibers may be of Kevlar ®, for example, which is virtually inextensible, thus lending tremendous resistance to bending deformation under load in the longitudinal direction, but still allowing collapsibility for delivery, deployment, and removal. Instead of fiber reinforcing, a further route to attaining strength with collapsibility is to add longitudinal reinforcing ribs to the polymer structure. These would give the added benefit of higher pressure capability due to reduced hoop stress, which in itself adds to the strength of the part, plus giving rigidity by virtue of the cross-sectional shape.

According to another aspect of the invention, a method of producing devices such as retractors with a collapsible, self-deploying end structure which has high load bearing capability over its entire projected surface is provided. Such devices can be manufactured using high strength engineering plastic or suitable metal open cell honeycomb or open cell foam structures. Suitable materials include, but are not limited to, aluminum or Aramid ® honeycomb structures from Hexcel ®. Such materials are normally utilized in their fully expanded configuration, are normally bonded between side members, and are not collapsible. According to the invention, however, the natural resilience of the proposed materials is utilized by collapsing the structures laterally, storing in a suitable delivery tube, and eventually ejecting from the delivery tube at the desired site. Upon ejection, the honeycomb structure springs out to its preferred configuration offering a large surface area suitable, by way of example, for manipulating internal bodily organs. Upon completion of the procedure, the device is merely withdrawn into its delivery tube, thus progressively collapsing the structure.

It has been found desirable to add a protective coating or membrane to the honeycomb to make it more atraumatic. Such coatings may be added by a conventional method, or an inflatable structure, such as the type described earlier, can be employed as a protective cover. A further method involves dipping the expanded honeycomb shape in natural rubber latex and curing the film formed. It has been found, surprisingly, that this process does not fill up the cells of the structure but, rather, forms a thin film across the top of the cells. In the cases wherein a film is bonded to the top and bottom surfaces of the cellular structure, it is necessary to drill very small holes in the interconnecting cell walls to allow trapped air or fluid to expel upon collapse and to allow air to enter the structure upon deployment.

In a further embodiment it has been found that the honeycomb structures described above can be machined to give, for example, curved shapes.

According to another embodiment of the invention, the inflatable device can comprise an isolation bag which represents a considerable improvement over existing devices. The isolation bag has a structure which can be deployed in a preferential orientation and held open by the application of slight pneumatic or hydraulic pressure to a series of interconnecting passages contained within a wall of the bag. The bag wall can include additional elements, such as wires of springy material as defined herein that will assist the bag in opening and maintaining its shape with or without pneumatic or hydraulic pressure.

By way of example, in one embodiment the bag can be manufactured from, for example, linear low density polyethylene films. These films can be welded together using any suitable method, as will be apparent to those skilled in the art (the preferred structure can be blow-molded, bonded, or formed using any other suitable process), irradiated to cross-link the polymer, heated above its crystalline melting point, distorted in the melted condition to a predominantly bag shape using, for example, a plunger or distorted by blowing with high pressure air into a shaped cavity, and cooled to below its crystalline melting point to impart structural stability. The channel in the neck area can be threaded with a thin wire of what is defined as "springy" material, such as pseudoelastic or superelastic shape memory alloy, fiber reinforced plastics, engineering plastics and other materials known to those skilled in the art that have sufficient flexibility and high yield strength that they do not permanently deform during deployment. These are the same materials that can be utilized in the bag wall as discussed above. The thin wire has sufficient strength to maintain the neck of the bag in a substantially round configuration yet is still easily collapsible. A small air or hydraulic pipe is bonded into the same channel. Alternatively, it may be especially mentioned that the wire and tube may be replaced by a hypotube of springy material as defined above which incorporates, for example, laser drilled holes near the distal end, thus forming a combined closing and inflation member.

The device can be carefully folded and inserted into a containment tube. Dimensions of the tube are suitable for insertion into, for example, the abdominal cavity via a trocar. Upon exiting the trocar, the device is ejected manually from its containment tube whereupon, for example, a wire of springy material in the neck region deploys the neck opening. Slight air or hydraulic pressure is now applied to the tube which penetrates into the channels formed between the welded sheets, and upon inflation, these channels force the isolation bag to take a preferred orientation, allowing the surgeon easy access for inserting the diseased tissue or organ. Upon completion, the channels in the bag are aspirated, allowing collapse. The wire in the neck region is drawn tight, thus closing the bag.

Further embodiments could utilize a drawstring which is attached to the end of the wire which is drawn through the channel by pulling out the wire of springy material. The drawstring is then used to close the bag, giving a superior closure. Additionally, the inner rim of the neck may be coated with a high tack polymer coating such as, for example, natural rubber latex to further ensure that there is no leakage of diseased cells. The bag can now be taken into the neck of the trocar and if not too full, be fully withdrawn. In cases where the organ is too large to exit the trocar, the bag may be worked out through the hole left by the trocar after its removal, or a morcellator may be introduced into the neck of the bag upon its exit from the trocar and the tissue reduced in size to allow final withdrawal.

A further embodiment of this device pertains to cases wherein very high strength is needed in the bag. In this instance, it is proposed that the bag be, for example, constructed of a fiber or cloth reinforced polymer. Among suitable materials there may be mentioned, but are not limited to, polyethylene polyester fabric or nylon fabric composites, natural rubber polyester fabric or nylon fabric composites, fabrics such as Goretex ®, and composites and laminates of suitable materials, as will be apparent to those skilled in the art.

In the case of reinforced materials, an alternative manufacturing process must be used, due to the inextensibility of the material. One such method would be to sew the article to the required shape, incorporating such ribs and channels as may be necessary, and to seal the stitching site with a suitable polymer, e.g., natural rubber latex. Another method would be to weld the structure using, for example, high frequency welding. Other methods will be apparent to those skilled in the art.

A further method of manufacture suited to structures manufactured from, for example, polyesters such as polyethylene terephthalate involves the molding of thin wall preforms which may be inserted one into the other and ribs incorporated via a suitable welding operation. One part may, in fact, have rib-like protuberances molded thereon which may be, for example, spun or ultrasonically welded to the mating part. Following the joining of the parts the structure may be expanded in size to form a much thinner wall structure by blowing to shape with high air pressure at a temperature between $T_g$ and $T_m$.

Various aspects of the invention are now described with reference to FIGS. 1-9.

As shown in FIG. 1, the medical device of the invention can comprise an inflatable retractor 1. Retractor 1 is inflatable by gas or liquid from a collapsed state, as shown in FIG. 1, to an expanded state, as shown in FIG. 2. Retractor 1 includes fluid actuating means including channels 2 and 3 which expand retractor 1 to the expanded state when pressurized gas or liquid is supplied thereto.

Retractor 1 can be introduced into a body cavity through tube 4. In particular, retractor 1 can be attached to hollow tube 5 which supplies fluid through passageway 5a to channels 2 and 3. Hollow tube 5 can include handle 6 for pushing and pulling retractor 1 along axis X outwardly and inwardly of a distal end of tube 4. Hollow tube 5 can include fitting 7 on a proximal end thereof for receiving a syringe or other device to supply pressurized fluid F to passageway 5a.

To facilitate movement of retractor 1 through tube 4, sliding carrier 8 can be provided at a distal end of hollow tube 5. Carrier 8 also seals passageway 5a to conduit 2 and provides a seal between an outer periphery thereof and an interior of tube 4 such as by means of annular channels and 0-rings around carrier 8. To facilitate collapsing of retractor 1 when pulled into tube 4, re-entry ferrule 9 can be provided at the distal end of tube 4. The ferrule 9 may contain internal spiral grooves to aid re-entry of retractor 1, the grooves folding the retractor 1 in orderly fashion.

Retractor 1 can include stiffening means such as ribs 10 and/or mechanical expansion means such as pre-bent wires 11. For instance, ribs 10 can comprise fully welded portions of the body of material used to form retractor 1. As shown in FIG. 2, ribs 10 can define channels 3 therebetween. Stiffening wires 11 can be pre-bent in a configuration closely resembling an outer periphery of retractor 1 in the expanded state. As shown in FIG. 2, when retractor 1 has a fan-shape in the expanded configuration, wires 11 can include a first portion parallel to a central axis of tube 4 and a second portion extending at an angle to the central axis. As shown in FIG. 1, when retractor 1 is collapsed, wires 11 are bent toward each other and fit within tube 4.

As shown in FIG. 3a, in the expanded state, retractor 1 can include flat planar section 1a parallel 5 to axis X and planar angled portion 1b extending at an angle to axis X at the distal end thereof. Angled portion 1b can be formed by appropriate selection of materials and/or fluid distribution channels in the body of material forming retractor 1.

It is within the scope of the invention to release a retractor in its expanded state within the body, thus leaving the trocar port available for other use. In such an embodiment the retractor 40, as seen in FIG. 3b, is releasably and recoverably connected to a carrier at the distal end 41 of the carrier. Any suitable valved, snap-connector device 42, such as those known to those skilled in the art, would define means to release and retrieve the retractor 40. Other inflatable members are also releasable and retrievable by such means. It is within the scope of the invention to conventionally modify the edges of the releasable retractor with complementary tongue (not shown) and groove 43 type structure. Other mating surfaces are also within the scope of the invention to interdigitate with like released retractors to form a multi-part structure within the body.

It is also within the scope of the invention to articulate a retractor by means of a pivotal joint 44 at the distal end of carrier 45 as seen in FIG. 3c. The movement of the retractor 46 can be controlled by a conventional push-pull control wire 47 within carrier 45. Inflation tube 48 is flexible in this instance.

FIGS. 4a-c show an embodiment wherein retractor 12 includes honeycomb reinforcing structure 13 and membrane 14 covering honeycomb reinforcing structure 13. FIG. 4a shows retractor 12 in the collapsed state, and FIG. 4b shows retractor 12 in the expanded state. As shown in FIG. 4c, the cell walls of honeycomb reinforcing structure 13 are closer together in the collapsed state than they are in the expanded state shown in FIG. 4b. In this case, retractor 12 need not include fluid actuating means to expand retractor 12 to its expanded state. Instead, reinforcing honeycomb structure 13 itself springs into the expanded configuration when retractor 12 is pushed outwardly of tube 4. However, membrane 14 can incorporate an inflated structure, such as conduit 2 and channels 3 described above with reference to FIGS. 1-3, in which case pressurized fluid F is supplied through hollow tube 5 to aid in expanding retractor 12 into its expanded configuration.

Figure 5B:
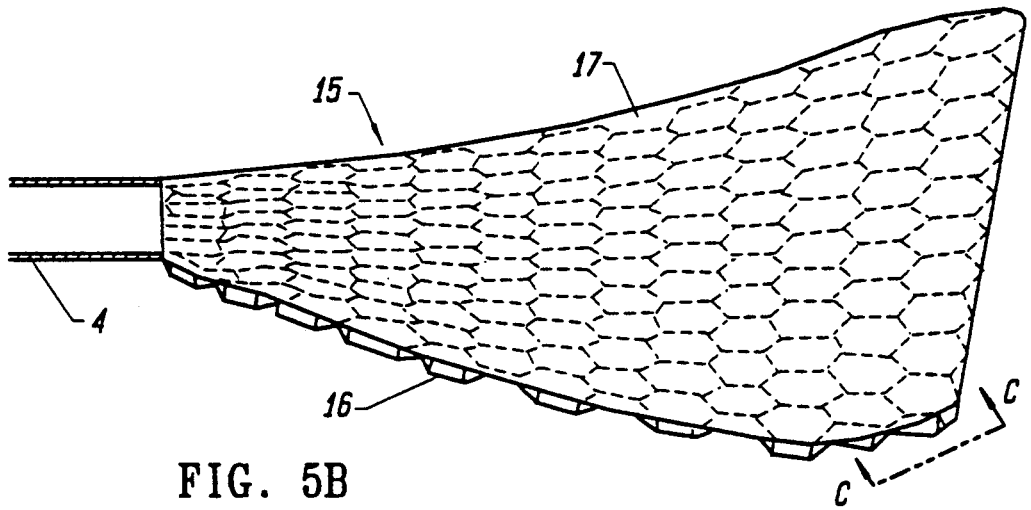
FIG. 5b shows the device of FIG. 5a with a bonded coating of natural rubber provided on a honeycomb reinforced structure of the device.
Figure 5C:
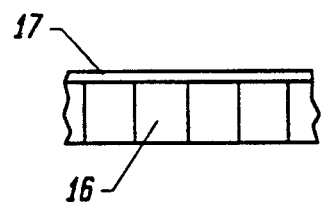
FIG. 5c is an enlargement of the encircled part C shown in FIG. 5b.
Figure 6A:
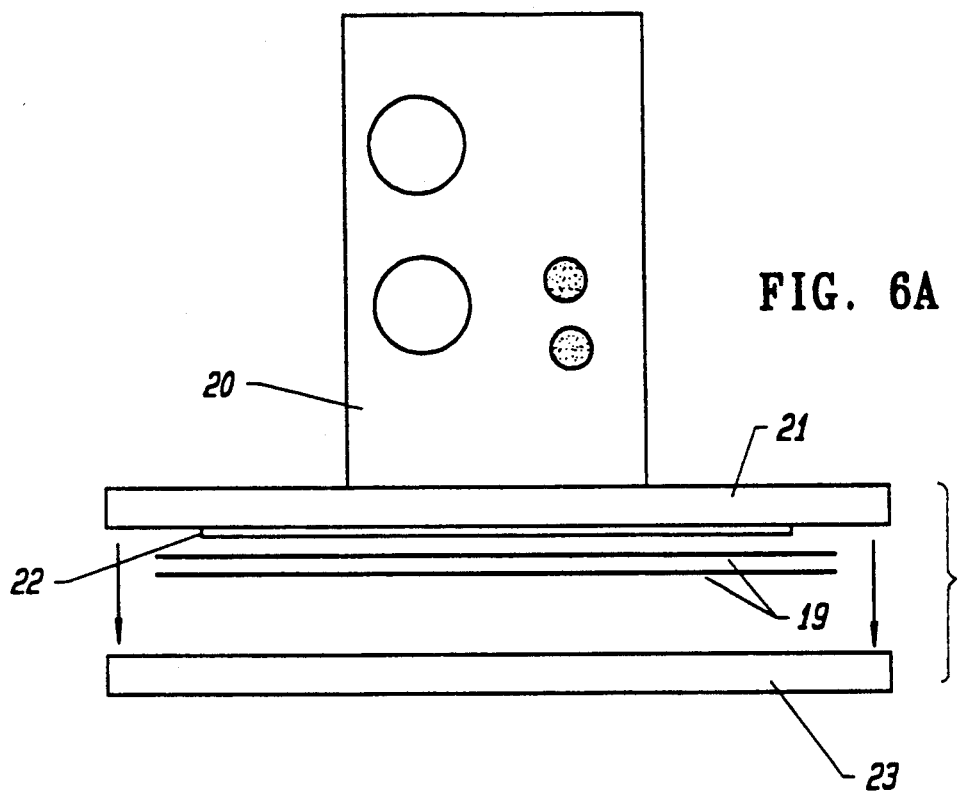
FIG. 6a shows equipment suitable for assembly of an isolation bag according to the invention from two films in a high frequency welder.
Figure 6B:
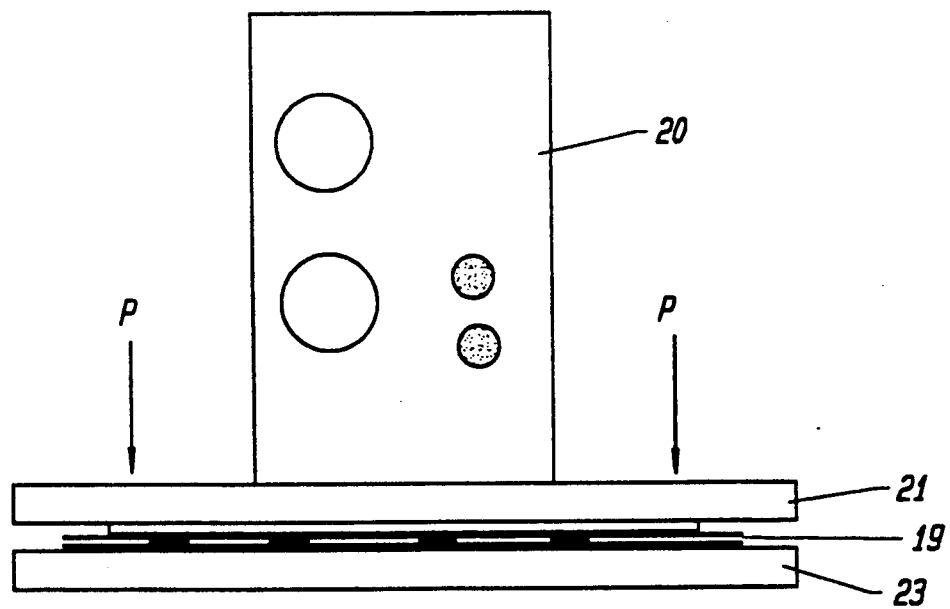
FIG. 6b shows the equipment of FIG. 6a during a bonding step.
Figure 7A:
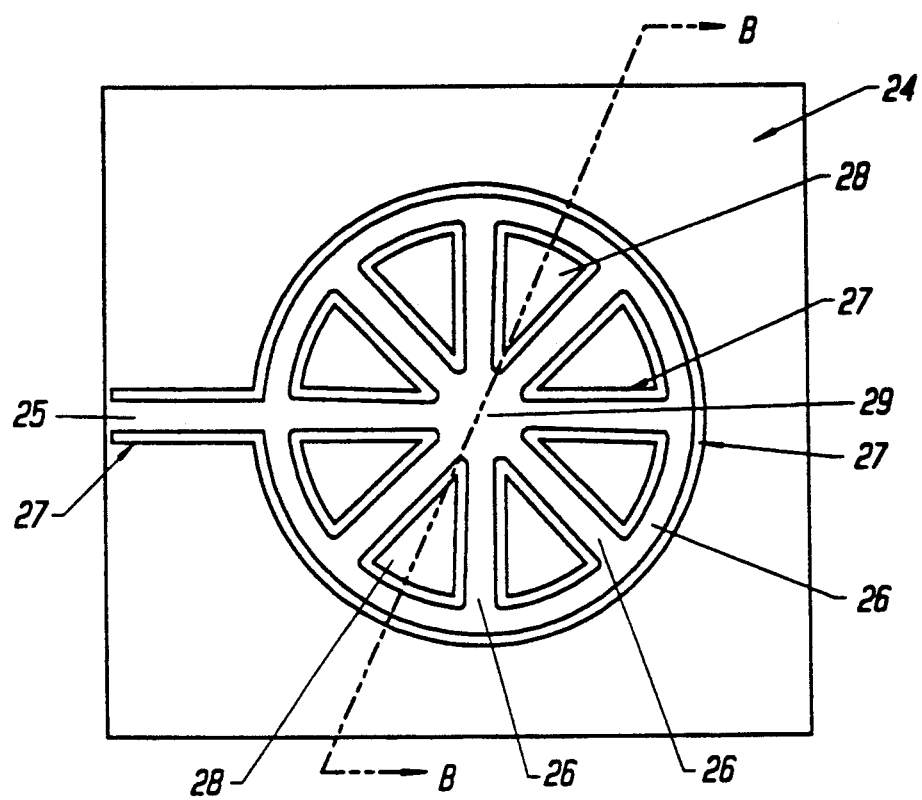
FIG. 7a shows a top view of one possible welded configuration which can be made with the equipment shown in FIGS. 6a-b.
Figure 7B:
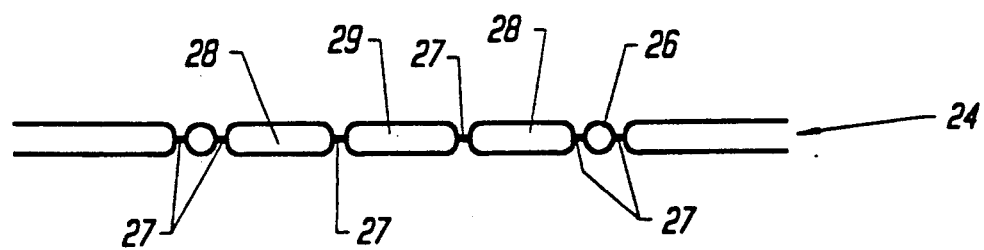
FIG. 7b shows a cross-section of the welded structure of FIG. 7a along the lines B-B.

FIGS. 5a-c show another embodiment of a honeycomb reinforced retractor 15 wherein the honeycomb is of a hexagonal or the like cell structure. In this case, retractor 15 can be deployed without fluid pressure. Instead, the natural resiliency of honeycomb reinforcing structure 16 causes retractor 15 to expand from the collapsed configuration of FIG. 5a to the expanded configuration of FIG. 5b. Honeycomb reinforcing structure 16 can be covered on one or both sides by membrane 17, as shown in FIG. 5c, which is an enlargement of detail C in FIG. 5b.

FIGS. 6-9 are directed to an embodiment of the invention wherein the medical device comprises isolation bag 18. Isolation bag 18 can be formed from two sheets of polymer films 19 which are bonded together by means of high frequency generator 20, upper platen 21, shaped die 22, and lower platen 23. FIG. 6a shows films 19 before they are bonded together, and FIG. 6b shows how films 19 are held between upper and lower platens 21 and 23, respectively, while pressure is applied thereto in the direction of arrows P. As a result, composite 24 is formed, as shown in FIGS. 7a and 7b.

Figure 8A:
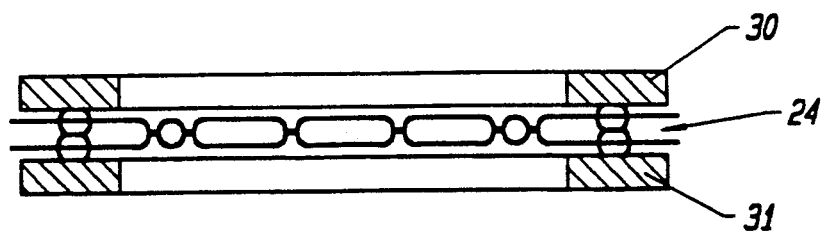
FIG. 8a shows a clamping device for the welded structure of FIGS. 7a-b.
Figure 8B:
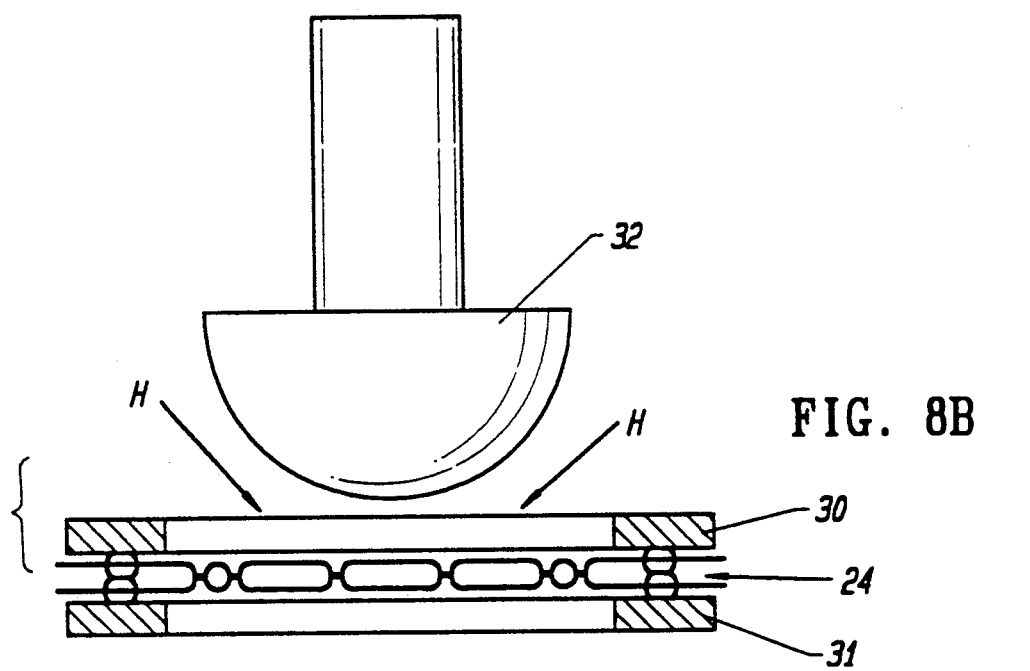
Figure 8C:
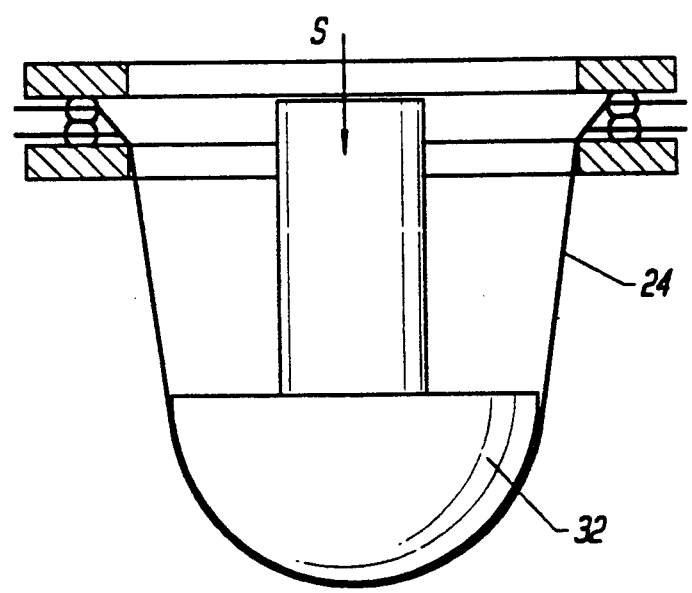
Figure 9:
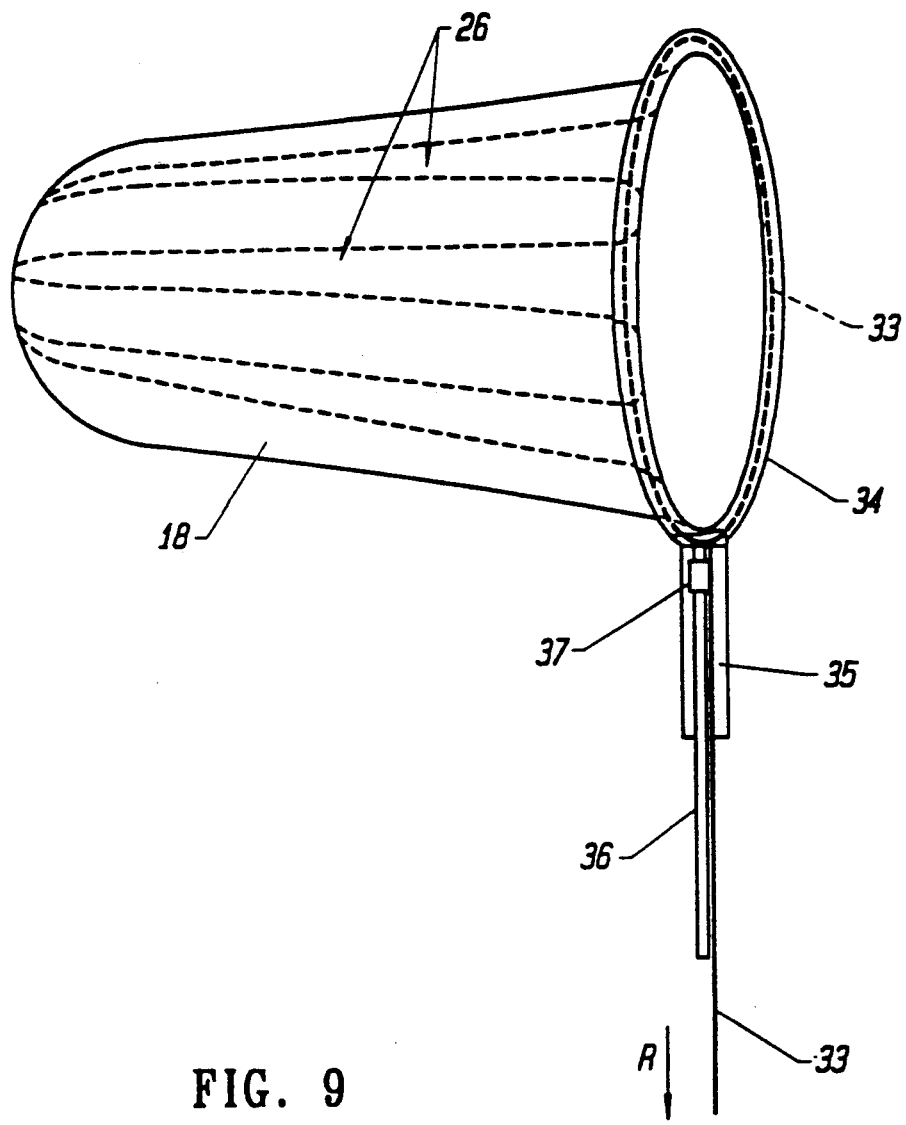
FIG. 9 shows a schematic of an isolation bag in accordance with one aspect of the invention.

Composite 24 includes conduit 25, channels 26, weld seams 27, dead air spaces 28 and central air space 29. It is understood that air spaces 28 are optional and that the films may be bonded together in that same area. FIGS. 8a-c show how composite 24 can be stretched into a shape suitable for isolation bag 18. First, composite 24 is clamped between upper clamping ring 30 and lower clamping ring 31, as shown in FIG. 8a. Then, heat is applied to composite 24 in the direction of arrows H (FIG. 8b), and plunger 32 is extended in the direction of arrow S to stretch composite 24 into the configuration shown in FIG. 8c. The result is a shape suitable for isolation bag 18, as shown in FIG. 9. In particular, isolation bag 18 includes fluid channels 26, and at an upper end thereof wire 33 of springy material as defined earlier formed into a loop extends through neck channel 34 of isolation bag 18. Isolation bag 18 can be introduced into a body cavity through tube 35. Inflation tube 36 supplies pressurized fluid to channels 26, and seal means 37 provides a seal between wire 33 and the interior of tube 35. Seal means 37 can be attached to wire 33 so as to travel therewith when isolation bag 18 is closed by retracting wire 33 in the direction of arrow R.

Although the invention has been described with reference to the foregoing embodiments, various changes and modifications can be made thereto which fall within the scope of the appended claims.

What is claimed is:

1. A medical device usable within a body cavity comprising:
an inflatable and collapsible retractor blade, the retractor blade having a first configuration in a collapsed state and a second configuration in an expanded state, the retractor blade including a substantially flat planar section in the expanded state, the the retractor blade being introducible into a body cavity by passing the retractor blade through a tube while the retractor blade is in the collapsed state, and the retractor blade being expandable from the first configuration to the second configuration when the retractor blade is inserted into the cavity beyond an end of the tube; and
fluid actuating means for expanding the retractor blade from the first configuration to the second configuration, the fluid actuating means comprising a conduit supported by the retractor blade, the retractor blade being expanded into the second configuration by supplying pressurized gas or liquid to the conduit.

2. The device of claim 1, wherein the retractor blade includes an atraumatic surface thereon.

3. The device of claim 1, wherein the retractor blade comprises a polymeric material selected from the group consisting of PVC, PVC copolymers, chlorinated polyethylene, ethylene ethyl acrylate copolymers, butadiene styrene block copolymers, polyethylene terephthalate, ionomers, polyisoprene, silicones, polyethylene, polyethylene copolymers, ethylene vinyl acetate copolymers, fluoropolymers, polyvinylidene fluoride, polyvinylidene fluoride copolymers, polypropylene copolymers, nylons such as but not limited to nylon 6.6, polyurethanes and other suitable polymers, blends and mixtures thereof.

4. The device of claim 1, wherein the retractor blade comprises a woven fabric or a sewn fabric having a fluid impervious coating.

5. The device of claim 1, wherein the fluid actuating means further comprises a plurality of fluid channels communicating with the conduit.

6. The device of claim 1, wherein the retractor blade includes reinforcing means supported by the retractor blade, the reinforcing means being selected from the group consisting of ribs and pre-shaped wire members.

7. The device of claim 1, further comprising an inner hollow tube attached to the retractor blade and an outer hollow tube for delivery of the retractor blade to a body cavity, the retractor blade having a distal end and a proximal end, the outer tube having a distal end and a proximal end, the retractor blade being slidable within the outer tube and being expandable to the second configuration at a position outwardly of the distal end of the outer tube, the distal end of the inner tube being attached to the proximal end of the retractor blade and the inner tube having a passageway communicating with the conduit of the retractor blade for inflation thereof.

8. The device of claim 7, further comprising a manually operable handle on a proximal end of the inner hollow tube, and a sliding carrier attached to the distal end of the inner hollow tube and providing a seal between an inner periphery of the inner tube and an inner periphery of the inner hollow tube.

9. A medical device usable within a body cavity comprising:
an inflatable and collapsible retractor blade, the retractor blade having a first configuration in a collapsed state and a second configuration in an expanded state, the retractor blade being introducible into a body cavity by passing the retractor blade through a tube while the retractor blade is in the collapsed state, and the retractor blade being expandable from the first configuration to the second configuration when the retractor blade is inserted into the cavity beyond an end of the tube; and
fluid actuating means for expanding the retractor blade from the first configuration to the second configuration, the fluid actuating means comprising a first and second conduits supported by the retractor blade, the retractor blade being expanded into the second configuration by supplying pressurized gas or liquid to the first and second conduits, the second conduit being discrete from and not in communication with the first conduit whereby the first conduit and the second conduit can each be supplied with pressurized fluid at different pressures.

10. A medical device usable within a body cavity comprising:
an outer hollow tube;
an inflatable and collapsible retractor blade, the retractor blade having a first configuration in a collapsed state and a second configuration in an expanded state, the retractor blade being introducible into a body cavity by passing the retractor blade through the outer tube while the retractor blade is in the collapsed state, and the retractor blade being expandable from the first configuration to the second configuration when the retractor blade is inserted into the cavity beyond a distal end of the outer tube;
fluid actuating means for expanding the retractor blade from the first configuration to the second configuration, the fluid actuating means comprising a conduit supported by the retractor blade, the retractor blade being expanded into the second configuration by supplying pressurized gas or liquid to the conduit;
an inner hollow tube for delivery of the retractor blade to a body cavity, the retractor blade having a distal end and a proximal end, the inner hollow tube having a distal end and a proximal end, the retractor blade being slidable within the outer hollow tube and being expandable to the second configuration at a position outwardly of the distal end of the outer hollow tube, the distal end of the inner hollow tube being attached to the proximal end of the retractor blade and the inner hollow tube having a passageway communicating with the conduit of the retractor blade for inflation thereof; and
means to release the inflatable and collapsible retractor blade from the inner hollow tube when the retractor blade is in its second configuration beyond the distal end of the outer hollow tube.

11. A medical device usable within a body cavity comprising:
an outer hollow tube;
an inflatable and collapsible retractor blade, the retractor blade having a first configuration in a collapsed state and a second configuration in an expanded state, the retractor blade being introducible into a body cavity by passing the retractor blade through the outer tube while the retractor blade is in the collapsed state, and the retractor blade being expandable from the first configuration to the second configuration when the retractor blade is inserted into the cavity beyond a distal end of the outer tube;

fluid actuating means for expanding the retractor blade from the first configuration to the second configuration, the fluid actuating means comprising a conduit supported by the retractor blade, the retractor blade being expanded into the second configuration by supplying pressurized gas or liquid to the conduit;

an inner hollow tube for delivery of the retractor blade to a body cavity, the retractor blade having a distal end and a proximal end, the inner hollow tube having a distal end and a proximal end, the retractor blade being slidable within the outer hollow tube and being expandable to the second configuration at a position outwardly of the distal end of the outer hollow tube, the distal end of the inner hollow tube being attached to the proximal end of the retractor blade and the inner hollow tube having a passageway communicating with the conduit of the retractor blade for inflation thereof; and means to release the inflatable and collapsible retractor blade from the inner hollow tube when the retractor blade is in its second configuration beyond the distal end of the outer hollow tube, the retractor blade including means to interdigitate the inflatable and collapsible retractor blade with another inflatable and collapsible retractor blade within a body cavity.

12. A medical device usable within a body cavity comprising:

an outer hollow tube;

an inflatable and collapsible retractor blade, the retractor blade having a first configuration in a collapsed state and a second configuration in an expanded state, the retractor blade being introducible into a body cavity by passing the retractor blade through the outer tube while the retractor blade is in the collapsed state, and the retractor blade being expandable from the first configuration to the second configuration when the retractor blade is inserted into the cavity beyond a distal end of the outer tube; and fluid actuating means for expanding the retractor blade from the first configuration to the second configuration, the fluid actuating means comprising a conduit supported by the retractor blade, the retractor blade being expanded into the second configuration by supplying pressurized gas or liquid to the conduit;

an inner hollow tube for delivery of the retractor blade to a body cavity, the retractor blade having a distal end and a proximal end, the inner hollow tube having a distal end and a proximal end, the retractor blade being slidable within the outer hollow tube and being expandable to the second configuration at a position outwardly of the distal end of the outer hollow tube, the distal end of the inner hollow tube being attached to the proximal end of the retractor blade and the inner hollow tube having a passageway communicating with the conduit of the retractor blade for inflation thereof; and means to articulate the inflatable and collapsible retractor blade beyond the distal end of the outer hollow tube.

* * * * *